United States Patent [19]

Franz

[11] 4,025,332

[45] May 24, 1977

[54] INCREASING SUCROSE CONTENT OF SUGARCANE PLANTS WITH N-PHOSPHONOMETHYLGLYCINAMIDES

[75] Inventor: John E. Franz, Crestwood, Mo.

[73] Assignee: Monsanto Company, St. Louis, Mo.

[22] Filed: Aug. 19, 1976

[21] Appl. No.: 715,778

Related U.S. Application Data

[63] Continuation-in-part of Ser. No. 510,923, Oct. 1, 1974, Pat. No. 3,988,142, which is a continuation-in-part of Ser. No. 223,351, Feb. 2, 1972, Pat. No. 3,853,530, which is a continuation-in-part of Ser. No. 123,057, March 10, 1971, abandoned.

[52] U.S. Cl. .................................... 71/86; 71/76
[51] Int. Cl.² ........................................ A01N 9/36
[58] Field of Search ................................ 71/86

[56] References Cited

UNITED STATES PATENTS

| 3,160,632 | 12/1964 | Fontoy et al. | 260/268 |
|---|---|---|---|
| 3,455,675 | 7/1969 | Irani | 71/86 |
| 3,556,762 | 1/1971 | Hamm | 71/86 |
| 3,726,947 | 4/1973 | Moser | 71/86 |
| 3,728,381 | 4/1973 | Randall | 71/86 |

*Primary Examiner*—Elbert L. Roberts
*Assistant Examiner*—Catherine L. Mills
*Attorney, Agent, or Firm*—Arnold H. Cole; Donald W. Peterson

[57] ABSTRACT

N-phosphonomethylglycinamides have been found to be useful in the treatment of sugarcane plants to increase their sucrose content.

14 Claims, No Drawings

INCREASING SUCROSE CONTENT OF SUGARCANE PLANTS WITH N-PHOSPHONOMETHYLGLYCINAMIDES

This application is a continuation-in-part of application Ser. No. 510,923, filed in Oct. 1, 1974, now U.S. Pat. No. 3,988,142, which is in turn a continuation-in-part of application Ser. No. 223,351, filed Feb. 2, 1972, now U.S. Pat. 3,853,530, which is in turn a continuation-in-part of application Ser. No. 123,057, filed Mar. 10, 1971, now abandoned.

This invention relates to a method for increasing the sucrose content of growing plants. More particularly, this invention is concerned with a method wherein sugarcane plants are subjected to a chemical treatment which serves to increase the amount of harvestable sucrose in said plants.

It has been found that certain N-phosphonomethylglycinamides, when applied to sugarcane plants in the manner hereinafter described, lead to an increase in the quantity of recoverable sucrose in such plants. Although not entirely certain, it is believed that this desirable effect results from the action of the amides to reduce or retard further vegetative growth of the plant after treatment. Thus, the reducing sugars which are stored in the plant are not expended as energy for added plant growth but are rather converted to recoverable sucrose.

The particular chemical compounds employed in the practice of the present invention are those of the formula

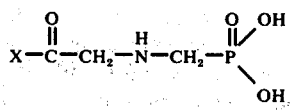

wherein X is morpholino, piperidino, pyrrolidino or NHR, and R is hydrogen, alkyl of 1 to 8 carbon atoms, lower alkenyl, cyclohexyl, hydroxyalkyl of 1 or 2 carbon atoms, or alkoxyalkyl of 3 or 4 carbon atoms.

As employed herein, the term "lower" designates those aliphatic hydrocarbon radicals which have up to 4 carbon atoms in a straight or branched chain. In the case of alkyl, the group begins with methyl, while the alkenyl group begins with vinyl. The hydroxyalkly radicals represented by R are hydroxymethyl and hydroxyethyl, while the alkoxyalkyl radicals are illustrated by methoxyethyl, methoxypropyl and ethoxyethyl.

Compounds of the above formula can be readily prepared by the procedures described in detail in applications Ser. No. 123,057, filed Mar. 10, 1971, Ser. No. 168,388, filed Aug. 2, 1971, both now abandoned, and Ser. No. 170,385, filed Aug. 9, 1971, now U.S. Pat. No. 3,799,758.

Specific representatives of the compounds which serve as active ingredients in the method of this invention include:

1. N-phosphonomethylglycinamide
2. N'-n-octyl-N-phosphonomethylglycinamide
3. N'-methyl-N-phosphonomethylglycinamide
4. N'-n-butyl-N-phosphonomethylglycinamide
5. N'-isopropyl-N-phosphonomethylglycinamide
6. N'-(2-hydroxyethyl)-N-phosphonomethylglycinamide
7. N'-(2-methoxyethyl)-N-phosphonomethylglycinamide
8. N'-cyclohexyl-N-phosphonomethylglycinamide
9. N'-allyl-N-phosphonomethylglycinamide
10. pentamethylene N-phosphonomethylglycinamide
11. tetramethylene N-phosphonomethylglycinamide
12. N-phosphonomethylglycine morpholide The specific tests which follow are presented as merely illustrative, non-limiting demonstrations of the useful and unexpected properties of various compounds of this invention.

EXAMPLE I

In determining the regulatory effects of compounds of this invention on sugarcane, it should be noted that the appropriate rate of application can vary from about 0.5 lb. per acre to about 5.0 lbs. per acre. Depending upon local cultural practices, sugarcane is grown for from about 9 to about 30 months before harvest, and it is thus necessary to consider both the chronological age and the maturity stage of the cane in rate determinations. Application of the treatment to the cane is generally made from about 2 to 10 weeks prior to the scheduled harvest date. Preferably, such applications are made from 3 to 7 weeks before said date.

In this test individual sugarcane stalks are treated with compounds of this invention about 4–5 weeks before harvest. To avoid sampling errors, older cane, preferably 13 to 23 months old, is employed in the tests. For each compound employed, at least 5 stalks are used, processed and the total values obtained are averaged for each stalk. In order to improve the accuracy of the analyses, only the terminal 15 joints of each stalk are used. An identical number of untreated sugarcane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in Hawaiian Planters' Record, Volume 57, pp. 133–150 (1964). The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugarcane juice.

About 38 mg. of each compound employed (on acid equivalent basis) is dissolved in a small amount of water which contains a small amount of a surface active agent. The resultant solution is then applied to the tip of each of the stalks to be tested with the exception of the untreated controls. At 4 or 5 weeks after treatment, the plants are harvested, and the top 15 joints of each stalk of a treated group are removed, combined and analyzed as described.

In order to convert a change in Pol percent Cane into a corresponding change in the quantity of sugar obtained, it is first necessary to know the average normal yield of sugar in the area under test. Here, the tests are carried out in a region where about 100 to 110 tons of cane are harvested per acre, and about 10 tons of sugar are obtained from this quantity of cane. With this average normal yield of 10 tons per acre, an increase of just 0.1 Pol percent Cane translates to an increase of about 200 pounds of sugar per acre.

The results obtained in tests with various compounds listed above are as follows:

HARVEST

| Compound | Four Weeks | | Five Weeks | |
|---|---|---|---|---|
| | Juice Purity | Pol % Cane | Juice Purity | Pol % Cane |
| 1 | 79.5 | 11.3 | 83.1 | 12.6 |
| 11 | 82.1 | 12.0 | 77.8 | 10.5 |
| Control | 77.2 | 9.9 | 69.8 | 7.9 |
| 9 | 87.8 | 13.6 | 86.4 | 13.2 |
| 12 | 83.9 | 11.9 | 86.0 | 12.5 |
| 4 | 79.0 | 9.7 | 74.8 | 9.2 |
| Control | 79.9 | 10.1 | 80.7 | 10.4 |

HARVEST

| Compound | Four Weeks | | Five Weeks | |
|---|---|---|---|---|
| | Juice Purity | Pol % Cane | Juice Purity | Pol % Cane |
| 8 | 82.8 | 11.0 | 75.3 | 9.6 |
| 3 | 89.3 | 13.6 | 83.3 | 12.6 |
| Control | 76.0 | 8.7 | 74.8 | 8.7 |
| 4 | 76.1 | 9.7 | 74.9 | 9.7 |
| Control | 75.5 | 9.0 | 77.6 | 9.4 |
| 3 | 85.5 | 13.2 | 85.8 | 13.9 |
| Control | 72.0 | 8.7 | 80.8 | 10.5 |
| 1 | 73.8 | 8.2 | 83.6 | 11.9 |
| 9 | 82.8 | 10.9 | 75.0 | 9.5 |
| 12 | 79.4 | 10.4 | 88.0 | 13.7 |
| Control | 78.4 | 9.1 | 66.2 | 7.8 |

EXAMPLE II

The testing procedures described in Example I are repeated with one of the compounds of this invention, and that compound is applied at several different rates. The results obtained are as follows:

HARVEST

| Compound | Rate mg./plant | Four Weeks | | Five Weeks | |
|---|---|---|---|---|---|
| | | Juice Purity | Pol % Cane | Juice Purity | Pol % Cane |
| 3 | 82 | 83.3 | 12.5 | 81.4 | 12.0 |
| | 41 | 81.2 | 11.3 | 76.9 | 9.9 |
| | 21 | 83.2 | 12.5 | 80.3 | 11.5 |
| | 11 | 82.4 | 12.8 | 76.3 | 9.5 |
| Control | — | 78.1 | 9.9 | 76.3 | 9.0 |

The active ingredients of this invention can, of course, be applied to the sugarcane plants in the free acid form shown in the formula above. Alternatively, such ingredients can be applied in the form of an agriculturally acceptable metal or amine salt. It is often found that a salt form improves such desirable features as stability or solubility, and these salts are prepared by methods illustrated in U.S. Pat. No. 3,799,758. Both mono and divalent metals can be employed at the salt-forming cation, while the amines can be primary, secondary or tertiary. Particularly preferred salts are those of the alkali metals, ammonia and the lower aliphatic hydrocarbon amines.

An active ingredient of this invention can be conveniently applied to the plants as an aqueous solution or suspension. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxy poly (ethyleneoxy) ethanols, polyethylene oxide adducts of fatty and resin acids, and long chain alkyl mercaptan adducts with ethylene oxide.

A particularly preferred carrier for the acids or salts of this invention is water with about 0.1 to 2.0 percent by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, the dilution being such that a spray volume of from about 7 to 20 gallons of liquid per acre will contain the desired dosage of active ingredient. It will be recognized, however, the higher or lower total spray volumes can be beneficially employed depending upon, the particular dispensing apparatus and other factors well understood by those skilled in the art. The exact amount of active ingredient to be employed is dependent upon such factors as the cane variety and stage of development thereof, and the environmental conditions, as well as the specific glycinamide employed. In general, the active ingredients are employed in effective sucrose increasing amounts equivalent to from about 0.5 to about 5.0 lbs./acre. It should be understood that the amount of active ingredient employed must be sufficient to increase the sucrose deposition in the treated plants without producing a herbicidal or killing effect on such plants. It is believed that those skilled in the art can readily determine from the teachings of this specification, including examples, the appropriate application rates.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A method for increasing the sucrose content of sugarcane plants which comprises applying to said plants, from about 2 to 10 weeks prior to harvest, an effective amount of a compound of the formula

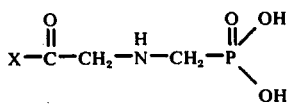

wherein X is morpholino, piperidino, pyrrolidino or NHR, and R is hydrogen, alkyl of 1 to 8 carbon atoms, lower alkenyl, cyclohexyl, hydroxyalkyl of 1 or 2 carbon atoms, or alkoxyalkyl of 3 or 4 carbon atoms.

2. A method as defined in claim 1 wherein application is made from about 3 to 7 weeks prior to harvest.

3. A method as defined in claim 1 wherein application is made at a rate of about 0.5 to 5.0 pounds per acre.

4. A method as defined in claim 1 wherein X is morpholino.

5. A method as defined in claim 1 wherein X is pyrrolidino.

6. A method as defined in claim 1 wherein X is NHR.

7. A method as defined in claim 6 wherein R is hydrogen.

8. A method as defined in claim 6 wherein R is alkyl of 1 to 8 carbon atoms.

9. A method as defined in claim 7 wherein R is methyl.

10. A method as defined in claim 7 wherein R is n-butyl.

11. A method as defined in claim 6 wherein R is allyl.

12. A method as defined in claim 6 wherein R is cyclohexyl.

13. A method for increasing the sucrose content of sugarcane plants which comprises applying to said plants, from about 2 to 10 weeks prior to harvest, an effective amount of a compound selected from those having the formula

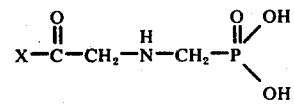

wherein X is morpholino, piperidino, pyrrolidino or NHR, and R is hydrogen, alkyl of 1 to 8 carbon atoms, lower alkenyl, cyclohexyl, hydroxyalkyl of 1 or 2 carbon atoms, or alkoxyalkyl of 3 or 4 carbon atoms; and the agriculturally acceptable salts thereof.

14. A method as defined in claim 13 wherein said salts are selected from alkali metals, ammonia, and lower aliphatic hydrocarbon amines.

* * * * *